(12) United States Patent
Neumann

(10) Patent No.: US 12,314,824 B2
(45) Date of Patent: May 27, 2025

(54) APPARATUS AND METHOD FOR GENERATING AN INGREDIENT CHAIN

(71) Applicant: KPN INNOVATIONS, LLC., Lakewood, CO (US)

(72) Inventor: Kenneth Neumann, Lakewood, CO (US)

( * ) Notice: Subject to any disclaimer, the term of this patent is extended or adjusted under 35 U.S.C. 154(b) by 0 days.

(21) Appl. No.: 18/410,814

(22) Filed: Jan. 11, 2024

(65) Prior Publication Data
US 2024/0144096 A1    May 2, 2024

Related U.S. Application Data

(63) Continuation-in-part of application No. 17/976,329, filed on Oct. 28, 2022, now Pat. No. 11,880,393.

(51) Int. Cl.
*G06F 16/00* (2019.01)
*G06F 16/28* (2019.01)
*G06N 20/00* (2019.01)

(52) U.S. Cl.
CPC .......... *G06N 20/00* (2019.01); *G06F 16/285* (2019.01)

(58) Field of Classification Search
CPC ................................... G06F 16/285
USPC ........................................... 707/737
See application file for complete search history.

(56) References Cited

U.S. PATENT DOCUMENTS

| | | | | |
|---|---|---|---|---|
| 10,262,030 B1 * | 4/2019 | Burtenshaw | ......... | G06F 16/289 707/707 |
| 2015/0032727 A1 * | 1/2015 | Chung | ............... | G06F 16/9538 707/722 |
| 2022/0012287 A1 * | 1/2022 | Sunkle | ................. | G06F 16/245 707/707 |

* cited by examiner

*Primary Examiner* — Alexandria Y Bromell
(74) *Attorney, Agent, or Firm* — Caldwell Intellectual Property Law

(57) ABSTRACT

In an aspect, an apparatus for generating an ingredient chain is presented. The apparatus includes at least a processor and a memory communicatively connected to the at least a processor. A memory contains instructions configuring at least a processor receive recipe data from a user. At least a processor is configured to extract a plurality of ingredients from recipe data. At least a processor is configured to classify, utilizing an ingredient classifier, a plurality of ingredients to a plurality of impact factors. At least a processor is configured to generate, as a function of impact factors, an ingredient chain for a user.

18 Claims, 5 Drawing Sheets

APPARATUS AND METHOD FOR GENERATING AN INGREDIENT CHAIN

CROSS-REFERENCE TO RELATED APPLICATIONS

This application is a continuation-in-part of Non-provisional application Ser. No. 17/976,329 filed on Oct. 28, 2022, and entitled "AN APPARATUS AND METHOD FOR GENERATING AN INGREDIENT CHAIN," the entirety of which is incorporated herein by reference.

FIELD OF THE INVENTION

The present invention generally relates to the field of ingredients and nutritional recipes. In particular, the present invention is directed to an apparatus and method for generating an ingredient chain.

BACKGROUND

Many factors may need to be accounted for when preparing a meal. However, many of these factors are unoptimized across a range of individuals. Therefore, generation of ingredient chains can be improved.

SUMMARY OF THE DISCLOSURE

In an aspect, an apparatus for generating an ingredient chain is presented. The apparatus includes at least a processor and a memory communicatively connected to the at least a processor. A memory contains instructions configuring at least a processor receive recipe data from a user. At least a processor is configured to extract a plurality of ingredients from recipe data. At least a processor is configured to classify, utilizing an ingredient classifier, a plurality of ingredients to a plurality of impact factors. At least a processor is configured to generate, as a function of impact factors, an ingredient chain for a user.

In another aspect, a method of generating an ingredient chain is presented. The method includes receiving, via at least a processor, recipe data from a user. The method includes classifying, via at least a processor and utilizing an ingredient classifier, a plurality of ingredients to a plurality of impact factors. The method includes generating, via at least a processor and as a function of impact factors, an ingredient chain for a user.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for generating ingredient chains. Aspects of the present disclosure can be used to generate ingredient chains. Aspects of the present disclosure can also be used to provide a graphical user interface for impact factors of ingredient chains.

Aspects of the present disclosure allow for classification of ingredients to impact factors. Exemplary embodiments illustrating aspects of the present disclosure are described below in the context of several specific examples.

Figure 1:
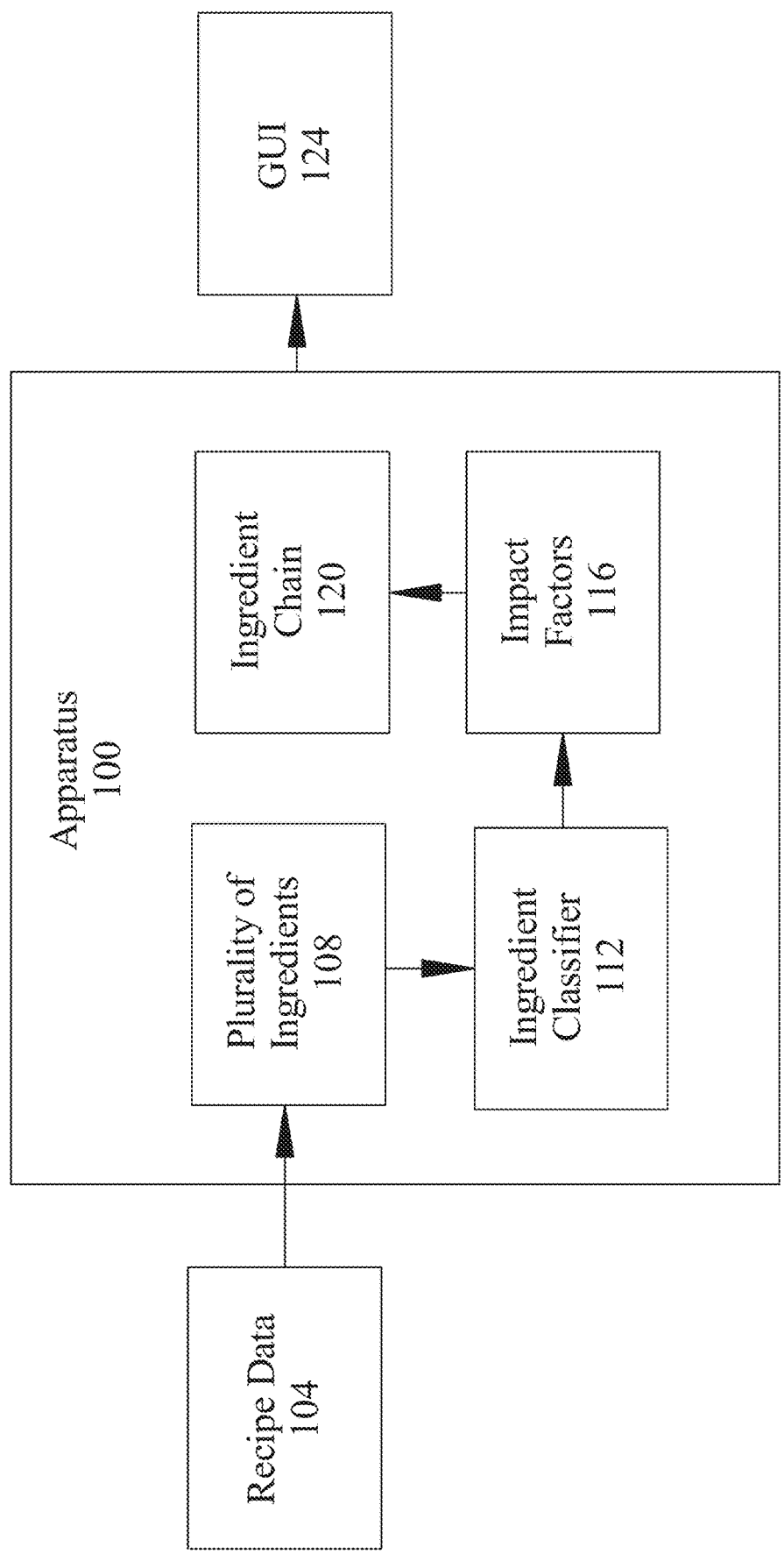
FIG. 1 is an exemplary embodiment of a block diagram of an apparatus for generating an ingredient chain.

Referring now to FIG. 1, an exemplary embodiment of an apparatus 100 for generating an ingredient chain is illustrated. Apparatus 100 may include a computing device. Apparatus 100 may include a processor and a memory communicatively connected to the processor. A memory may include instructions configuring at least a processor to perform various tasks. As used in this disclosure, "communicatively connected" means connected by way of a connection, attachment, or linkage between two or more related which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Apparatus 100 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Apparatus 100 may include a single computing device operating independently, or may include two or more computing device operating in concert, in parallel, sequentially or the like; two or more computing devices may be included together in a single computing device or in two or more computing devices. Apparatus 100 may interface or communicate with one or more additional devices as described below in further detail via a network interface device. Network interface device may be utilized for connecting apparatus 100 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Apparatus 100 may include but is not limited to, for example, a computing device or cluster of computing devices in a first location and a second computing device or cluster of computing devices in a second location. Apparatus 100 may include one or more computing devices dedicated to data storage, security, distribution of traffic for load balancing, and the like. Apparatus 100 may distribute one or more computing tasks as described below across a plurality of computing devices of computing device, which may operate in parallel, in series, redundantly, or in any other manner used for distribution of tasks or memory between computing devices. Apparatus 100 may be implemented using a "shared nothing" architecture in which data is cached at the worker, in an embodiment, this may enable scalability of apparatus 100 and/or computing device.

With continued reference to FIG. 1, apparatus 100 may be designed and/or configured to perform any method, method step, or sequence of method steps in any embodiment described in this disclosure, in any order and with any degree of repetition. For instance, apparatus 100 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Apparatus 100 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, in some embodiments, apparatus 100 may be configured to receive recipe data 104. "Recipe data" as used in this disclosure is information pertaining to a consumable good. A "consumable good" as used in this disclosure is any edible item or items. Consumable goods may include, but are not limited to, food, drinks, and the like. In some embodiments, a meal may include one or more consumable goods, such as, without limitation, drinks, snacks, entrees, breakfasts, lunches, dinners, and the like. In some embodiments, recipe data 104 may include a meal identification. A "meal identification," also referred to as meal id, as used in this disclosure, is a classification of a recipe. In some embodiments, apparatus 100 may receive recipe data 104 and/or a meal ID from a user. A "user," as used in this disclosure, is any individual. In some embodiments, a meal id of recipe data 104 may include a title and/or a description related to a meal. For example a meal ID may include a name of a dish, such as "Beef Stroganoff". A description of a meal ID may include one or more general contents of a dish and/or a specific description of the dish. For example, a description may include data that Beef Stroganoff is an originally Russian dish of sautéed pieces of beef served in a sauce of mustard and smetana (sour cream). Still referring to FIG. 1, apparatus 100 is configured to receive recipe data containing nutrient data from the user. Recipe data may include a list of ingredients to prepare a meal. For example, and without limitation, recipe data 104 may include ingredients in a beef stroganoff dish, which may include: 1 pound uncooked wide egg noodles, ¼ cup butter, divided, 2½ pounds thinly-sliced steak, fine sea salt and freshly-cracked black pepper, 4.5 small white onions, thinly sliced, 3 pound sliced mushrooms, 2 cloves garlic, minced or pressed, ½ cup dry white wine, 1½ cups beef stock, 1 tablespoon Worcestershire sauce, 3 tablespoons all-purpose flour, ½ cup of sour cream, and chopped fresh parsley.

Still referring to FIG. 1, in some embodiments, apparatus 100 may extract plurality of ingredients 108 from recipe data 104. A "plurality of ingredients" as used in this disclosure is one or more parts of a recipe. "Ingredients," as used in this disclosure, are elements of a meal. Ingredients may include, but are not limited to, meats, vegetables, sauces, syrups, seafoods, fruits, dairy products, and the like. In some embodiments, apparatus 100 may utilize a language processing module to extract plurality of ingredients 108 from recipe data 104. A language processing module may include any hardware and/or software module. A language processing module may be configured to extract, from the one or more documents, one or more words, letters, characters, and the like, without limitation. One or more words may include, without limitation, strings of one or more characters, including without limitation any sequence or sequences of letters, numbers, punctuation, diacritic marks, engineering symbols, geometric dimensioning and tolerancin (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, a language processing module may operate to produce a language processing model. A language processing model may include a program automatically generated by computing device and/or a language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

Still referring to FIG. 1, a language processing module and/or diagnostic engine may generate the language processing model by any suitable method, including without limitation a natural language processing classification algorithm; a language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating a language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, a language processing module may use a corpus of documents to generate associations between language elements in a language processing module, and diagnostic engine may then use such associations to analyze words extracted from one or more documents and determine that the one or more documents indicate significance of a category. In an embodiment, language module and/or apparatus 100 may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into apparatus 100. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York.

Still refereeing to FIG. 1, in some embodiments, apparatus 100 may utilize optical character recognition to identify and/or extract plurality of ingredients 108 from recipe data 104. Optical character recognition or optical character reader (OCR) includes automatic conversion of images of written (e.g., typed, handwritten or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases. a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 1, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

Still referring to FIG. 1, in some embodiments, recipe data 104 may be provided by a user, such as, but not limited to, a chef, line cook, an individual, and the like. Recipe data 104 may be received and/or stored by a graphical user interface or a user database as described further below. Alternatively or additionally, apparatus 100 may retrieve recipe data 104 from an online repository or other suitable source for retrieving information regarding meal preparation. In non-limiting illustrative examples, recipe data 104 may contain sequentially ordered tasks that may be sequentially ordered based upon a chronological order, tasks ordered by resource optimization, and the like. Recipe data 104 may contain elements, steps, instructions, or the like that refer to preparing one or more meals, by one or more personnel, using one of more stations, appliances, utensils, and the like. In non-limiting illustrative examples, apparatus 100 may retrieve a plurality of recipe data 104 by retrieving a series of steps corresponding to a meal id, for instance and without limitation, recipe steps using available ingredients for cooking a beef stew. In further non-limiting illustrative examples, the steps to a beef stew may be associated with a chronological sequential ordering of personnel tasks, ingredient retrieval, kitchen space use, and may differ based upon time constraints, including and/or avoiding certain ingredients, equipment, and the like.

Still referring to FIG. 1, in some embodiments, apparatus 100 may be configured to generate a web search. A "web search" as used in this disclosure is a query for information through the Internet. Generating a web search may include generating a web crawler function. A web search may be configured to search for one or more keywords, key phrases, and the like. A keyword may be used by a query to filter potential results from a query. As a non-limiting example, a keyword may include "Gluten". A query may be configured to generate one or more key words and/or phrases as a function of recipe data 104. A query may give a weight to one or more semantic elements of recipe data 104. "Weights", as used herein, may be multipliers or other scalar numbers reflecting a relative importance of a particular attribute or value. A weight may include, but is not limited to, a numerical value corresponding to an importance of an element. In some embodiments, a weighted value may be referred to in terms of a whole number, such as 1, 100, and the like. As a non-limiting example, a weighted value of 0.2 may indicate that the weighted value makes up 20% of the total value. As a non-limiting example, recipe data 104 may include the words "gluten free". A query may give a weight of 0.8 to the word "gluten", and a weight of 0.2 to the word "free". A query may map a plurality of semantic elements of query results having similar elements to the word "gluten" with differing elements than the word "free" due to the lower weight value paired to the word "gluten". In some embodiments, a query may pair one or more weighted values to one or more semantic elements of recipe data 104. Weighted values may be tuned through a machine-learning model, such as any machine learning model as described throughout this disclosure without limitation. In some embodiments, a query may generate weighted values based on prior queries. In some embodiments, a query may be configured to filter out one or more "stop words" that may not convey meaning, such as "of," "a," "an," "the," or the like.

Still referring to FIG. 1, in some embodiments, apparatus 100 may generate an index classifier. In an embodiment, an index classifier may include a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. An index classifier may include a classifier configured to input semantic elements and output web search indices. A "web search index," as defined in this disclosure is a data structure that stores uniform resource locators (URLs) of web pages together with one or more associated data that may be used to retrieve URLs by querying the web search index; associated data may include keywords identified in pages associated with URLs by programs such as web crawlers and/or "spiders." A web search index may include any data structure for ordered storage and retrieval of data, which may be implemented as a hardware or software module. A web search index may be implemented, without limitation, as a relational database, a key-value retrieval datastore such as a NOSQL database, or any other format or structure for use as a datastore that a person skilled in the art would recognize as suitable upon review of the entirety of this disclosure. Data entries in a web search index may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a web search index may reflect categories, cohorts, and/or populations of data consistently with this disclosure. In an embodiment, a web search query at a search engine may be submitted as a query to a web search index, which may retrieve a list of URLs responsive to the query. In some embodiments, apparatus 100 may be configured to generate a query based on a freshness and/or age of a query result. A freshness may include an accuracy of a query result. An age may include a metric of how outdated a query result may be. In some embodiments, apparatus 100 may generate a web crawler configured to search the Internet for recipe data 104, such as, but not limited to, ingredients, preparation steps, category of food, allergen data, and the like. As a non-limiting example, a query may include a web crawler configured to search and/or index information of words and/or phrases having a similarity to recipe data 104.

Still referring to FIG. 1, in some embodiments, recipe data 104 may include nutrient data. "Nutrient data," as used in this disclosure, is information pertaining to the nutritional value of one or more ingredients. In some embodiments, nutrient data may include nutritional values related to ingredients in a meal. For example, nutritional values may include the value of vitamin, caloric, protein, fat, cholesterol, sugar, carbohydrate, sodium, and the like in the meal. For example, in beef stroganoff, the nutritional values may be calories 235, total fat 11 g, saturated fat 6 g, cholesterol 50 mg, sodium 1,044 mg, potassium 336 mg, total carbohydrate 22 g, dietary fiber 1.4 g, sugar 4 g, protein 12 g, vitamin c. In some embodiments, nutritional values may include a daily value of nutrients in a dish. "Daily value (DV)," as used in this disclosure, is the recommended amount of nutrients a person should consume and not to exceed each day. The % DV may be how much a nutrient in a single serving of an individual dish or dietary supplement contributes to a daily diet. For example, if the DV for a certain nutrient is 300 micrograms (mcg) and a dish or supplement has 30 mcg in one serving, the % DV for that nutrient in a serving of the product may be 10%. In some embodiments, apparatus 100 may receive recipe data from a user database. User database may contain recipe data received from a plurality of different users categorized to a common meal id. For example, user database may contain a recipe data table containing a plurality of different recipes and nutritional values common for a beef stroganoff dish.

Still referring to FIG. 1, in some embodiments, apparatus 100 may be configured to classify plurality of ingredients 108 to impact factors 116. An "impact factor," as used in this disclosure, is a metric of influence one or more ingredients has on an individual's biological system. A "biological system" as used in this disclosure is a process and/or group of processes that occur in an individual's physiology. Impact factors 116 may include, without limitation, concentration of nutrients, quantity of nutrients, calories of ingredients, allergens associated with one or more ingredients, carbohydrate and/or other macronutrient quantities, ratios, and the like. In some embodiments, impact factors 116 may be based on essential macronutrients and micronutrients. "Micronutrients," as used herein, are nutrients that a person needs in small doses. For example, micronutrients may include vitamins and minerals. "Macronutrients," as used herein, are nutrients that a person needs in larger amounts. For example, macronutrients may include water, protein, carbohydrates, and fats. In some embodiments, impact factors 116 may be based on nutrients essential for boosting the immune system, helping prevent or delay certain cancers, such as prostate cancer, strengthening teeth and bones, aiding in calcium absorption, maintaining healthy skin, helping the body metabolize proteins and carbs, supporting healthy blood, burning fat, building muscle, maintaining weight, losing water weight, aiding brain and nervous system functioning, aiding in blood clotting, helping to carry oxygen and/or the like. A user may select, through GUI 124, what impact factors 116 may be based on. In some embodiments, a user may select a plurality of impact factors 116. In some embodiments, receive impart factor data in the form of documents, medical papers, research papers, and the like through an impact factors 116 database. "Impact factor database," as used in this disclosure, is a data structure containing information related to a plurality of impact factors 116. An impact factor database may be populated by apparatus 100 utilizing a web crawler. An impact factor database may be populated by expert submission. An "expert," as used herein, is a person who has a comprehensive and authoritative knowledge of or skill in a particular area. For example, a doctor may submit a paper on how fish oil aids in preventing cancer. An expert submission may include a single expert submission and/or a plurality of submissions from an expert; plurality of submissions may be received from a plurality of experts as described in U.S. patent application Ser. No. 16/397,814, filed, Apr. 29, 2019, and titled "METHODS AND SYSTEMS FOR CLASSIFICATION USING EXPERT DATA", of which is incorporated by reference herein in its entirety.

Still referring to FIG. 1, in some embodiments, apparatus 100 may determine one or more impact factors 116 for one or more phenotypes. A "phenotype," as used in this disclosure, is a composite observable characteristic or trait of an individual. A phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Phenotype may include a congenital disorder, anomaly, and the like, such as hearing defects, trisomy 18 (Edward's syndrome), trisomy 21 (down syndrome), trisomy 13 (Patau syndrome), cleft palate, spina bifida, phenylketonuria, glutamate carboxypeptidase II mutation, pyloric stenosis, congenital hip dislocation, anencephaly, hypoplasia, Meckel's diverticulum, and the like. Phenotype may include a genotype-environment interaction (GxE). Phenotype may include any diagnosis (current disorder) and/or prognosis (predicted difficulty, future diagnosis, outcome, and the like) associated with a congenital factor. Phenotype may include identifiers associated with disorders, conditions, symptoms, and the like, which may correspond with categorization. Phenotype may include a predictive classification, where a subject may be considered reasonably healthy at birth, does not harbor congenital factor(s) indicative of obvious current congenital disorder but may include data that indicates a phenotype with which they may be most closely categorized to, and/or an imminent categorization. A phenotype may be stored and/or retrieved from a user database.

Still referring to FIG. 1, in some embodiments, apparatus 100 may classify plurality of ingredients 108 to impact factors 116 utilizing an ingredient classifier 112. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. Ingredient classifier 112 may be configured to output at least a datum that labels or otherwise identifies a set of data that are clustered together, found to be close under a distance metric as described below, or the like. In some embodiments, ingredient classifier 112 may receive meal ID and recipe data as an input and output a plurality of matched nutrient data elements to an importance factor. For example, ingredient classifier 112 may match ingredients in a dish that contain a nutritional value that are essential for boosting the immune system. In some embodiments, ingredient classifier 112 may receive meal ID and recipe data as an input and output a plurality of matched nutrient data elements to a plurality of impact factors. For example, ingredient classifier 112 may match ingredients in a dish that contain a nutritional value that are essential for boosting the immune system, building muscle, maintaining healthy skin, and the like. Training data for ingredient classifier 112 may include data from impart factor data. For example, classification based on muscle building may include training data containing documents and expert submission exemplifying nutrients that may correlate to muscle building. In some embodiments, training data may include, a plurality of recipe data received from a plurality of user from user database.

Still referring to FIG. 1, in some embodiments, apparatus 100 may receive recipe data 104 and/or a meal ID from a user database. A "user database," as used in this disclosure is a data structure contain information uploaded by a user. User database may contain information from a plurality of different users categorized to a common meal id. For example, user database may contain a meal ID table containing a plurality of different titles common for a beef stroganoff dish and a plurality of different meal descriptions associated to the dish. User database and all other databases in this disclosure may be implemented, without limitation, as a relational user database, a key-value retrieval user database such as a NOSQL user database, or any other format or structure for use as a user database that a person skilled in the art would recognize as suitable upon review of the entirety of this disclosure. User database may alternatively or additionally be implemented using a distributed data storage protocol and/or data structure, such as a distributed hash table or the like. User database may include a plurality of data entries and/or records as described above. Data entries in a user database may be flagged with or linked to one or more additional elements of information, which may be reflected in data entry cells and/or in linked tables such as tables related by one or more indices in a relational user database. Persons skilled in the art, upon reviewing the entirety of this disclosure, will be aware of various ways in which data entries in a user database may store, retrieve, organize, and/or reflect data and/or records as used herein, as well as categories and/or populations of data consistently with this disclosure. A user database may include one or more elements of recipe data 104 and/or user data. In some embodiments, a user database may be populated through user input and/or one or more web searches.

Still referring to FIG. 1, in some embodiments, ingredient classifier 112 may be further configured to score plurality of ingredients 108. Ingredient classifier 112 may score plurality of ingredients 108 across a plurality of phenotypes to determine an impact factor of impact factors 116. In some embodiments, ingredient classifier 112 may be configured to score a plurality of nutrients of plurality of ingredients 108. Scores may be based off, without limitation, relative impact of one or more nutrition elements on one or more phenotypes. For instance, and without limitation, a score of 3 out of 10 may be assigned to a filet mignon for a phenotype of vegan. In some embodiments, a score may be based off a nutrition target range. Apparatus 100 may be configured to receive and/or determine a nutrition target range of one or more users, phenotype groups, and the like. A "nutrition target range," as used in this disclosure, is a value or range of values of quantities of nutrients. Apparatus 100 may utilize a nutrient target machine learning model to determine a nutrient target range of one or more individuals. A nutrient target machine learning model may be trained with training data correlating user data to nutrition target ranges. Training data may be received through user input, external computing devices, and/or previous iterations of processing. In some embodiments, ingredient classifier 112 and/or apparatus 100 may utilize a nutrient target machine learning model. A nutrient target machine learning model may be configured to receive user data and/or recipe data 104 and output one or more nutrient target ranges of one or more individuals and/or groups of individuals.

Still referring to FIG. 1, computing device may be configured to generate a nutrition supplement as a function of the nutrition range target. A "nutrition supplement," as used in this disclosure, is a modification of a recipe. Nutritional supplements may include, without limitation, different sets of ingredients, such as spices, meats, seasonings, vitamin powders, and the like. In some embodiments, ingredient classifier 112 may be configured to receive training data correlating recipe data and/or user data to one or more nutritional supplements. Training data may be received through user, external computing devices, and/or previous iterations of processing. Ingredient classifier 112 may input recipe data 104 and/or user data and output one or more nutritional supplements. suggested by computing device that offer nutritional values aligned to nutrition range target.

Still referring to FIG. 1, in some embodiments, apparatus 100 may be configured to generate ingredient chain 120. An "ingredient chain" as used in this disclosure is a set of edible items. Edible items may include, without limitation, seasonings, spices, vitamin powders, meats, seafood, fruits, vegetables, dairy products, and the like. In some embodiments, apparatus 100 may compare impact factors 116 with plurality of ingredients 108 to generate ingredient chain 120. In some embodiments, apparatus 100 may be configured to compare any data as described throughout this disclosure using an objective function. For instance, apparatus 100 may generate an objective function. An "objective function" as used in this disclosure is a process of minimizing or maximizing one or more values based on a set of constraints. In some embodiments, an objective function of apparatus 100 may include an optimization criterion. An optimization criterion may include any description of a desired value or range of values for one or more impact factors; desired value or range of values may include a maximal or minimal value, a range between maximal or minimal values, or an instruction to maximize or minimize an impact factor. As a non-limiting example, an optimization criterion may specify that an impact factor should be within a 1% difference of an optimization criterion. An optimization criterion may alternatively request that an impact factor be greater than a certain value. An optimization criterion may specify one or more tolerances for differences in macronutrients of one or more ingredients in a recipe. An optimization criterion may specify one or more desired impact factor criteria for an ingredient chain. In an embodiment, an optimization criterion may assign weights to different impact factors or values associated with impact factors. One or more weights may be expressions of value to a user of a particular outcome, impact factor value, or other facet of an ingredient chain. Optimization criteria may be combined in weighted or unweighted combinations into a function reflecting an overall outcome desired by a user; function may be an ingredient chain function to be minimized and/or maximized. A function may be defined by reference to impact factor criteria constraints and/or weighted aggregation thereof as provided by apparatus 100; for instance, an impact factor function combining optimization criteria may seek to minimize or maximize a function of ingredient chain generation.

Still referring to FIG. 1, generation of an objective function may include generation of a function to score and weight factors to achieve a process score for each feasible pairing. In some embodiments, pairings may be scored in a matrix for optimization, where columns represent ingredients and rows represent impact factors potentially paired therewith; each cell of such a matrix may represent a score of a pairing of the corresponding ingredient to the corresponding impact factor. In some embodiments, assigning a predicted process that optimizes the objective function includes performing a greedy algorithm process. A "greedy algorithm" is defined as an algorithm that selects locally optimal choices, which may or may not generate a globally optimal solution. For instance, apparatus 100 may select pairings so that scores associated therewith are the best score for each impact factor and/or for each ingredient. In such an example, optimization may determine the combination of ingredients such that each impact factor pairing includes the highest score possible.

Still referring to FIG. 1, an objective function may be formulated as a linear objective function. Apparatus 100 may solve an objective function using a linear program such as without limitation a mixed-integer program. A "linear program," as used in this disclosure, is a program that optimizes a linear objective function, given at least a constraint. For instance, and without limitation, objective function may seek to maximize a total score $\Sigma_{r \in R}\Sigma_{s \in S} c_{rs} x_{rs}$, where R is a set of all ingredients r, S is a set of all impact factors s, $c_{rs}$ is a score of a pairing of a given ingredient with a given impact factor, and $x_{rs}$ is 1 if an ingredient r is paired with an impact factor s, and 0 otherwise. Continuing the example, constraints may specify that each ingredient is assigned to only one impact factor, and each impact factor is assigned only one ingredient. Impact factors may include ingredients as described above. Sets of ingredients may be optimized for a maximum score combination of all generated ingredients. In various embodiments, apparatus 100 may determine a combination of ingredients that maximizes a total score subject to a constraint that all ingredients are paired to exactly one impact factor. Not all impact factors may receive an ingredient pairing since each impact factor may only produce one ingredient pairing. In some embodiments, an objective function may be formulated as a mixed integer optimization function. A "mixed integer optimization" as used in this disclosure is a program in which some or all of the variables are restricted to be integers. A mathematical solver may be implemented to solve for the set of feasible pairings that maximizes the sum of scores across all pairings; mathematical solver may be implemented on apparatus 100, another device, and/or may be implemented on third-party solver.

With continued reference to FIG. 1, optimizing an objective function may include minimizing a loss function, where a "loss function" is an expression an output of which an optimization algorithm minimizes to generate an optimal result. As a non-limiting example, apparatus 100 may assign variables relating to a set of parameters, which may correspond to score ingredients as described above, calculate an output of mathematical expression using the variables, and select a pairing that produces an output having the lowest size, according to a given definition of "size," of the set of outputs representing each of a plurality of ingredients and/or impact factors; size may, for instance, included absolute value, numerical size, or the like. Selection of different loss functions may result in identification of different potential pairings as generating minimal outputs. Objectives represented in an objective function and/or loss function may include minimization of impact factors. Objectives may include minimization of preparation time of a recipe. Objectives may include minimization of costs of a recipe. Objectives may include maximization of compatibility across a wide range of individuals.

Still referring to FIG. 1, in some embodiments, apparatus 100 may receive meal ID through a graphical user interface (GUI) 124. A "graphical user interface" as used in this disclosure is an interface including a set of one or more pictorial and/or graphical icons corresponding to one or more computer actions. GUI 124 may be configured to receive user input, as described above. GUI 124 may include one or more event handlers. An "event handler" as used in this disclosure is a callback routine that operates asynchronously once an event takes place. Event handlers may include, without limitation, one or more programs to perform one or more actions based on user input, such as generating pop-up windows, submitting forms, changing background colors of a webpage, and the like. Event handlers may be programmed for specific user input, such as, but not limited to, mouse clicks, mouse hovering, touchscreen input, keystrokes, and the like. For instance and without limitation, an event handler may be programmed to generate a pop-up window if a user double clicks on a specific icon. User input may include, a manipulation of computer icons, such as, but not limited to, clicking, selecting, dragging and dropping, scrolling, and the like. In some embodiments, user input may include an entry of characters and/or symbols in a user input field. A "user input field" as used in this disclosure is a portion of a graphical user interface configured to receive data from an individual. A user input field may include, but is not limited to, text boxes, search fields, filtering fields, and the like. In some embodiments, user input may include touch input. Touch input may include, but is not limited to, single taps, double taps, triple taps, long presses, swiping gestures, and the like. One of ordinary skill in the art will appreciate the various ways a user may interact with GUI 124. In some embodiments, GUI 124 may be consistent with graphical user interfaces as described in U.S. patent application Ser. No. 17/062,740, filed Oct. 5, 2020, and titled "METHODS AND SYSTEMS FOR ARRANGING AND DISPLAYING GUidED REC-OMMENDATIONS VIA A GRAPHICAL USER INTERFACE BASED ON BIOLOGICAL EXTRACTION", of which is incorporated by reference herein in its entirety.

Continuing in reference to FIG. 1, apparatus 100 may retrieve a plurality of ingredient chain 120, wherein retrieving an ingredient chain 120 may include retrieving, for each meal of the plurality of meals, an ingredient chain 120 identifying a plurality of sequentially ordered tasks for preparation of the meal. An ingredient chain may be provided by a user, such as a restaurant, cook, or the like, and ingredient chains may be stored and/or retrieved by apparatus 100 from a meal database, for instance from an ingredient chain database. Alternatively or additionally, apparatus 100 may retrieve ingredient chains 120 from an online repository or other suitable source for retrieving information regarding meal preparation. In non-limiting illustrative examples, an ingredient chain may contain sequentially ordered tasks that may be sequentially ordered based upon a chronological order, tasks ordered by resource optimization, task ordered by customer priority, and the like. An ingredient chain may contain elements, steps, instructions, or the like that refer to preparing one or more meals, by one or more personnel, using one of more stations, appliances, utensils, and the like. Apparatus 100 may store and/or retrieve ingredient chain 120, or an element of an existing ingredient chain 120 to form a new ingredient chain 120, from a meal database, online repository, blog, culinary website, or any other suitable source, as described above. In non-limiting illustrative examples, apparatus 100 may retrieve a plurality of ingredient chains 120 by retrieving a series of steps corresponding to an identification of a meal of recipe data 104, for instance and without limitation, recipe steps using available ingredients for cooking a beef stew. In further non-limiting illustrative examples, the steps to a beef stew may be associated with a chronological sequential ordering of personnel tasks, ingredient retrieval, kitchen space use, and may differ based upon time constraints, including and/or avoiding certain ingredients, equipment, and the like.

Continuing in reference to FIG. 1, apparatus 100 may retrieve a plurality of ingredient chains 120, wherein retrieving may include identifying, for each ingredient chain 120, a resource list identifying a plurality of resources, wherein each resource is associated with a task of the plurality of sequentially ordered tasks. A "resource list," as described in this disclosure refers to a tabulation, list, or the like, of ingredient identities, amounts, and expirations; kitchen stations, equipment, appliances, utensils, dishware, personnel, operating hours, tables, customers; delivery couriers including restaurant employees and secondary couriers via application services, 'gig' economy services, and the like; delivery vehicles, including cars, trucks, bikes, and the like, and any other suitable resource relating the preparation of a meal, delivery of a meal, and/or meal orders. Apparatus 100 may determine a resource and tabulate, list, group, or otherwise categorize a plurality of resources by retrieving a resource form a database, as described above. Alternatively or additionally, a resource of a resource list may be stored and/or retrieved from a database by a machine-learning process, such as a first machine-learning model, as a resource may correspond to a plurality of meals, ingredients, ingredient chains, or the like.

Still referring to FIG. 1, in some embodiments, apparatus 100 may retrieve and/or generate a plurality of ingredient chains 120. Ingredient chains 120 may differ at branching points that correspond to different pathways, series of elements, steps, or the like in preparing a meal. In non-limiting illustrations a branch point may represent places where deviations in tasks in an ingredient chain 120 may differ for instance, omitting or including a step to eliminate or add a new ingredient, for instance removing onions from the beef stew upon customer request, or customizing meal by adding chives. In further non-limiting illustrative examples, a branch point may represent a place in an ingredient chain 120 where concurrently performed steps are added, subtracted, combined, or split into new ingredient chain 120. For instance and without limitation, a branch point may include a beginning preparation of a beef stock for a meal, a first kitchen personnel may include next any series of vegetables, beginning with any of the four, before moving to a next task in the ingredient chain 120. In such an example, several ingredient chain 120 modifications may be introduced at the branch point, for instance and without limitation, a second kitchen personnel may be added to assist in the ingredient preparation steps to decrease time of meal preparation, or a fifth ingredient may be added upon request to customize a meal further, resource permitting. Ingredient chains 120 may be listed in a sequentially ordered manner and mapped to the anticipated timescale for preparing a meal; timescale may be altered by applying different resource lists to different steps in ingredient chain 120 and/or modifying ingredient chain 120 by adding/subtracting branch points, removing/adding tasks, and the like. For instance and without limitation, a plurality of ingredient chains 120 may be mapped to a 12-hr time scale for preparing a beef stew, wherein a negative time value represents "time out" from a meal being finished, and a positive time value represents "time post preparation," including for example delivery time, customer retrieval time, and the like. Ingredient chain 120 may be optimized, combined, and or otherwise modified as described in further detail below to decrease average time of preparation.

Referring still to FIG. 1, apparatus 100 may generate a plurality of candidate ingredient chain combinations, wherein each ingredient chain combination may include a first ingredient chain of the plurality of ingredient chains and a second ingredient chain of the plurality of ingredient chains, and a first task of the first ingredient chain and a second task of the second ingredient chain are concurrently performed using a resource associated with each of the first task and the second task. A first task of a first ingredient chain and a second task of a second ingredient chain may be placed in a sequentially ordered sequence and/or performed concurrently relative to each other depending on constraints on task ordering and/or combination. For instance, a first task of a first ingredient chain may be to prepare a first meal at a station and a second task of a second ingredient chain may be to prepare a second meal, wherein the first meal introduces an allergen to be excluded from the second meal; this would introduce a constraint that would limit the sequential ordering in this manner. In such an example, the sequential order of the two different ingredient chains would need to be changed based on avoiding said allergen. In further non-limiting illustrative examples, a first task of a first ingredient chain may be to prepare 1 cup of a first ingredient and a second task of a second ingredient chain may be to prepare 1 cup of that same ingredient, a first task of a first ingredient chain and a second task of a second ingredient chain may be combined concurrently to improve efficiency, wherein a single person may prepare 2 cups at once. Determining if any constraint exists may include determining if a constraint would limit a first task of a first ingredient chain being ordered followed by a second task in a second ingredient chain in either a sequential and/or concurrent ordering. If either ingredient chain ordering is determined to be allowed based upon constraints, then ordering of a plurality of ingredient chains may be added to a feasible list for further feasibility quantifier analysis, as described in further detail below. In non-limiting illustrative examples, a plurality of ingredient chain 120 may be concurrently listed, for instance combined into a plurality of candidate ingredient chain combinations determined by sequentially listing certain tasks and concurrently performing other tasks within a potential combination of ingredient chains, wherein concurrently performed tasks overlap at least for a moment in time, personnel, station, equipment, or overlap in any resource, as described above. In further non-limiting illustrative examples, concurrently performed tasks of two ingredient chains may involve, for instance and without limitation, a combination of resource at once such as preheating an oven of a first ingredient chain, washing utensils to remove allergens of a second ingredient chain, and chopping vegetables of a third ingredient chain. In such a non-limiting example, a first ingredient chain may correspond to preparing two distinct meals, such as a second meal and third meal, each of which may require heating in an oven at the same temperature, or at an average temperature suitable for both meals while using a single oven, wherein the average temperature is an optimized temperature calculated by a machine-learning model and/or objective function to batch cooking steps together, as described in further detail below; a second ingredient chain may correspond to removing allergens from a first meal that can be done while preparing a second meal and a third meal, but must be completed prior to finishing the preheating stage; a third ingredient chain may correspond to chopping vegetables that may correspond to an ingredient preparation task that overlaps with a plurality of meals.

Continuing in reference to FIG. 1, ingredient chains 120 and candidate ingredient chain combinations may include signifiers, numerical values, alphanumerical codes, and the like that contain elements of data regarding identifiers related to certain combinations of ingredient chains elements, resource amounts, time amounts, constraints, and/or any other identifiable parameters that may be used in determining feasibility of an ingredient chain, or plurality of ingredient chain combinations, as described in further detail below. A machine-learning model may, for instance, retrieve ingredient chain 120 from a meal database and determine feasibility of said ingredient chain 120 by identification by a signifier, as described above.

Continuing in reference to FIG. 1, apparatus 100 may identify a plurality of constraints as a function of identifications of meals, which may include at least a resource constraint and at least a timing constraint. A "constraint," as used herein refers to a barrier, limitation, consideration, or any other constraint pertaining to resource utilization during optimizing the combination of a plurality of ingredient chains that may arise during meal preparation and/or delivery as a function of performing a plurality of ingredient chains combinations, wherein the constraint may alter the time and/or resources available to preparing a meal or performing a task, may alter the concurrent and/or sequential ordering of tasks in a plurality of ingredient chains, and/or may alter the feasibility of combining a plurality of ingredient chains. Constraints may be identified by an optimization process during optimization of ingredient chain combinations 124, as described in further detail below. A constraint may, for instance and without limitation, only appear during a particular optimized listing of a plurality of ingredient chain elements, wherein a second listing of the same elements in a different ordering may not show the same constraint. In non-limiting illustrative examples, a constraint may be a resource constraint, wherein dedicating an individual to a series of tasks for preparing a meal would then place a constraint on preparing a second meal with said individual, or performing a second combination of ingredient chains; likewise a constraint may be a time constraint wherein the maximal time allotted for selecting ingredient chains for an individual or set of individuals working in tandem in preparing a meal may be dictated by when a customer places an order, whether a customer is dine-in or take-out, delivery method for the meal, and/or type of meal and ingredients used. Constraints may refer to customer preferences, for instance and without limitation, such as the presence of allergies, food intolerances, hypersensitivities, or other dietary constraints, philosophical, religious, and/or moral considerations to ingredients and/or meal preparation, and the like; constraints may refer to seasonality of ingredients, ingredient amounts, ingredient substitutions, and/or other material and immaterial constraints to ingredient availability and use. Such information may be stored and/or retrieved by apparatus 100 from a database, for instance, via orders input by a restaurant wait staff, logged by a web based application, mobile application, or other meal ordering service, application, device, of the like. Meal orders may be provided in a non-electronic format and ingredient chain 120 retrieved after a user prompts apparatus 100 for ingredient chain 120 associated with an order, which may contain constraint information. Constraint information may be stored and/or retrieved alongside ingredient chain 120 information by use of an alphanumeric code, numerical value, or any other method of signifying the presence, amount, and/or nature of a constraint related to a task, ingredient chain 120, and/or combinations of ingredient chain 120.

Continuing in reference to FIG. 1, apparatus 100 may be configured to generate plurality of candidate ingredient chain combinations by receiving feasibility training data. Feasibility training data may include a plurality of entries correlating task combinations with feasibility quantifiers. A "feasibility quantifier," as used in this disclosure is a score, metric, function, vector, matrix, numerical value, or the like, which describes a qualitative and/or quantitative mathematical proportion, propensity, or any relationship correlating the likelihood, possibility, and/or probability of completing a task, given a set of constraints and the a task's relationship in time to and ordering to other tasks, within a particular timeframe, wherein a timeframe may be determined by an identification of a meal, meal preparation time, expected delivery time, resource list, ingredient chain 120, and the like. Apparatus 100 may identify feasible combinations based on various constraints, wherein apparatus 100 may find and/or set values for those constraints or add a new constraint in the form of a "feasibility quantifier". In non-limiting illustrative examples, a feasibility quantifier may include scores relating the probability of feasibility for completing a series of tasks, wherein each task has an associated probability in relating preparation of a beef stew related to preparing the beef stew for a customer order within, for instance, a 15-minute time frame, 30-minute time frame, 1-hour time frame, etc. In further non-limiting illustrative examples, ingredient chain steps that would require more than a 15-minute time frame would garner scores indicating lower levels of feasibility, such as for instance placing beef in a marinade, chopping vegetables, and cooking a beef stock, and thus may result in candidate ingredient chain steps that would sequentially order meal preparation of such steps for a suitable amount of time prior to the 15-minute time frame. Additionally, in non-limiting illustrative examples, ingredient chain steps that could be completed within the 15-minute time frame of ordering may include combining the ingredients, and plating the meal, which would garner higher feasibility scores resulting in ingredient chain elements that may be combined in such a way that allows an individual to complete the entire ingredient chain combination to fulfill orders within 15 minutes of the customer placing the order. Feasibility quantifiers may be stored and/or retrieved from a database. Alternatively or additionally, determining the feasibility of an ingredient chain may include resource constraint information, as described in further detail below, wherein the feasibility of an individual completing a first candidate ingredient chain combination depends upon if that same individual is dedicated to a second candidate ingredient chain combination, and if the suitable kitchenware, utensils, appliances, workstations, and the like, are in use and/or if preparation of the next meal may result in an biological and/or philosophical conflict for a customer, for instance an allergy to peanuts, a lactose-free meal after cooking with milk, Kosher preparation, or a vegan meal. Feasibility quantifiers may incorporate information, for instance, if there would be enough time to prepare a second meal after a first meal, if a second meal would demand decontamination of a common space to avoid antigen cross-contamination. In such a non-limiting illustrative example, a feasibility quantifier may rank a candidate ingredient chain combination in such a way that gave a more favorable score to preparing a second meal first, followed by a first meal, as described in further detail below.

With continued reference to FIG. 1, apparatus 100 may be configured to generate a recipe machine-learning model. A "recipe machine-learning model," as used in this disclosure, is a mathematical representation of a relationship between inputs and outputs, as generated using any machine-learning process and/or machine-learning algorithm including without limitation any process as described herein, and stored in memory; an input is submitted to a machine-learning model once created, which generates an output based on the relationship that was derived. Generating recipe machine-learning model may include calculating one or more supervised machine-learning algorithms including active learning, classification, regression, analytical learning, artificial neural network, backpropagation, boosting, Bayesian statistics, case-based learning, genetic programming, Kernel estimators, naïve Bayes classifiers, maximum entropy classifier, conditional random field, K-nearest neighbor algorithm, support vector machine, random forest, ordinal classification, data pre-processing, statistical relational learning, and the like. Generating recipe machine-learning model may include calculating one or more unsupervised machine-learning algorithms, including a clustering algorithm such as hierarchical clustering, k-means clustering, mixture models, density based spatial clustering of algorithms with noise (DB SCAN), ordering points to identify the clustering structure (OPTICS), anomaly detection such as local outlier factor, neural networks such as autoencoders, deep belief nets, Hebbian learning, generative adversarial networks, self-organizing map, and the like. Generating recipe machine-learning model may include calculating a semi-supervised machine-learning algorithm such as reinforcement learning, self-learning, feature learning, sparse dictionary learning, anomaly detection, robot learning, association rules and the like. Recipe machine-learning model is trained by apparatus 100 using training data, including any of the training data as described herein. Training data may be obtained from records of previous iterations of generating recipe machine-learning model, user inputs and/or questionnaire responses, expert inputs, and the like. Recipe machine-learning model may be implemented as any machine-learning process, including for instance, and without limitation, as described in U.S. Nonprovisional application Ser. No. 16/375,303, filed on Apr. 4, 2019, and entitled "SYSTEMS AND METHODS FOR GENERATING ALIMENTARY INSTRUCTION SETS BASED ON VIBRANT CONSTITUTIONAL GUIDANCE," the entirety of which is incorporated herein by reference. Recipe machine-learning model is trained using training data to select recommended refreshments favored by a user selection. In an embodiment, user selection contained within a selection database may be utilized as training data to customize and train recipe machine-learning model individually for each user. For instance and without limitation, user selection that indicate a user prefers to eat foods that contain protein choices that contain either chicken, tofu or salmon and the user dislikes protein choices that contain beef or pork may be utilized as training data to generate recommended refreshments such as chicken picada, tofu and green bean stir fry, and miso glazed salmon, and to not generate recommended refreshments such as a ground beef stir fry or a pork burger. In another embodiment, recipe machine-learning model may output a plurality of recommended refreshments as a function of the health condition of the user. For instance and without limitation, a user may have a gluten allergy. In this example, recipe machine-learning model may output recommended refreshment suitable for the user where the recommended refreshment are gluten-free.

Still referring to FIG. 1, in some embodiments, apparatus 100 may determine one or more additional ingredients. Additional ingredient may be classified to plurality of impact factors 116. An additional ingredient may include an ingredient not extracted from recipe data 104. Apparatus 100 may identify an additional ingredient as a function of plurality of ingredients 108. For example, an additional ingredient may include an ingredient which pairs well with one or more ingredients of plurality of ingredients 108. In another example, an additional ingredient may include an ingredient which is interchangeable with one or more ingredients of plurality of ingredients 108. In some embodiments, apparatus 100 may identify an additional ingredient based on a health and/or nutrition benefit of the additional ingredient. For example, apparatus 100 may identify an additional ingredient from a predetermined list of ingredients, such as healthy ingredients.

Still referring to FIG. 1, in some embodiments, apparatus 100 may determine an impact factor of a plurality of potential additional ingredients as described above. Apparatus 100 may select an additional ingredient from a plurality of potential additional ingredients based on an impact factor. For example, additional ingredients associated with impact factors which are considered health benefits may be selected and/or additional ingredients associated with impact factors which are considered health detriments may be avoided.

Still referring to FIG. 1, in some embodiments, apparatus 100 may display additional ingredient to user. As used herein, a device "displays" a datum if the device outputs the datum in a format suitable for communication to a user. For example, a device may display a datum by outputting text or an image on a screen or outputting a sound using a speaker. For example, apparatus 100 may display additional ingredient to a user as a suggestion and may give user options as to whether to accept and/or reject such suggestion. For example, an additional ingredient that is healthier than an ingredient of plurality of ingredients 108 may be generated and displayed to a user as a suggested replacement.

Still referring to FIG. 1, in some embodiments, apparatus 100 may receive a response from a user. As used herein, a "response" is an action taken based on communication of an additional ingredient to a user, a datum generated based on communication of an additional ingredient to a user, or both. For example, a response may include an indication from a user as to whether an additional ingredient should be included. In some embodiments, a user device is used to communicate with a user. A user device may include, in non-limiting examples, a smartphone, tablet, or computer. In some embodiments, a chatbot is used to communicate with a user. In some embodiments, a language model is used to interpret data received from a user and/or user device. Data analyzed using a language model may include, in a non-limiting example, data gathered as a freeform user input rather than, for example, a selection between 2 options. In some embodiments, a language model is used to generate data which is displayed to a user, such as communications identifying an additional ingredient. In some embodiments, data displayed to a user may be generated using templates into which data such as names of ingredients may be input. Apparatus 100 may generate one or more follow up communications as a function of a response and/or display such communications to user.

Still referring to FIG. 1, in some embodiments, apparatus 100 may determine an additional ingredient based on availability of such ingredient and/or ease of obtaining such ingredient. In non-limiting examples, apparatus 100 may determine an additional ingredient based on geographic availability of ingredients, time availability of ingredients, when ingredients are in season, when locations which provide ingredients are open, and which ingredients a user already has. Apparatus 100 may be configured to receive data describing ingredients a user has. Such data may be received from a user device, such as a smartphone, tablet, or computer. A user may input ingredients using an interactive element of a user interface, such as a button, touchscreen, mouse, keyboard, microphone, and the like. User input into a user device may configure the user device to transmit to apparatus 100 a signal indicating which ingredients a user has.

Still referring to FIG. 1, in some embodiments, ingredient chains 120 may be ranked based on availability of ingredients. In non-limiting examples, apparatus 100 may rank ingredient chains based on geographic availability of ingredients, time availability of ingredients, when ingredients are in season, when locations which provide ingredients are open, which ingredients a user already has, and which ingredients are readily available to a user. Whether an ingredient is readily available may be determined based on, for example, a combination of factors described herein as being associated with availability. For example, whether an ingredient is readily available may be based on a combination of geographic availability, when the ingredient is in season, and when a location which provides the ingredient is open. Rankings may be determined based on number of ingredients which are sufficiently available, cost of ingredients which are not sufficiently available, percent of ingredients which are sufficiently available, and the like. In some embodiments, apparatus 100 may rank a first ingredient chain and a second ingredient chain, determine an ingredient chain ranking as a function of the availability of ingredients of the first ingredient chain and the second ingredient chain; and display to a user the ingredient chain ranking.

Still referring to FIG. 1, in some embodiments, ingredient chains may be categorized. Non-limiting examples of categorizations include soups, snacks, and dinner meals. Such ingredient chain categories may be used to filter ingredient chains and/or determine which ingredient chains are generated. A category preference may be gathered and used to determine an ingredient chain. As used herein, a "category preference" is a datum generated based on a user input indicating a user preference for, or aversion to, an ingredient chain category. In some embodiments, apparatus 100 may prevent an ingredient chain of a certain ingredient chain category from being generated. In some embodiments, apparatus 100 may generate an ingredient chain from a certain ingredient chain category. For example, a category preference may indicate that a user does not desire salads or beverages, and apparatus 100 may prevent ingredient chains from these categories from being generated and/or may filter such ingredient chains out. In some embodiments, generating an ingredient chain may include categorizing an ingredient chain to an ingredient chain category; receiving a category preference from the user; and comparing the ingredient chain category to the category preference. In some embodiments, categorizing an ingredient chain to an ingredient chain category may be done using an ingredient chain category classifier. An ingredient chain category classifier may be trained using a supervised learning algorithm. An ingredient chain category classifier may be trained on a training dataset including a plurality of example ingredient chains as inputs correlated to a plurality of example ingredient chain categories as outputs. Once trained, ingredient chain category classifier may be used to identify an ingredient chain category by inputting an ingredient chain and receiving an ingredient chain category as an output.

Still referring to FIG. 1, in some embodiments, apparatus 100 may determine an ingredient chain as a function of a preparation time. For example, a user may select a preparation time limit, and apparatus 100 may generate ingredient chains with estimated preparation times under such limit. In some embodiments, a user may input a desired preparation time, a desired preparation time range, a desired maximum preparation time, or the like, and apparatus 100 may determine an ingredient chain with a compatible preparation time. In some embodiments, apparatus 100 may determine a preparation time based on other data associated with a user, such as ingredient chains selected and/or prepared by the user in the past, ratings of ingredient chains by the user, ingredient chains selected and/or prepared by similar users, or ratings of ingredient chains by similar users.

Still referring to FIG. 1, in some embodiments, apparatus 100 may determine an ingredient chain as a function of a preparation skill datum. As used herein, a "preparation skill datum" is a datum describing an experience level relevant to food preparation, a skill level relevant to food preparation, or both, associated with a user. A preparation skill datum may be received from a user. In some embodiments, a user may input a preparation skill level or experience level of the user. In some embodiments, a user may input a desired preparation skill level. For example, a highly skillful user may wish to prepare a simple ingredient chain. Apparatus 100 may determine a preparation skill datum based on such a user input. In some embodiments, apparatus 100 may determine a preparation skill datum based on other data associated with a user, such as ingredient chains selected and/or prepared by the user in the past, ratings of ingredient chains by the user, ingredient chains selected and/or prepared by similar users, or ratings of ingredient chains by similar users.

Still referring to FIG. 1, in some embodiments, apparatus 100 may receive an ingredient chain selection datum from a user; and store an ingredient chain associated with the ingredient chain selection datum in a database as a function of the ingredient chain selection datum. Apparatus 100 may later display such stored ingredient chains to a user, such as upon user selection of an interactive element associated with saved ingredient chains.

Figure 2:
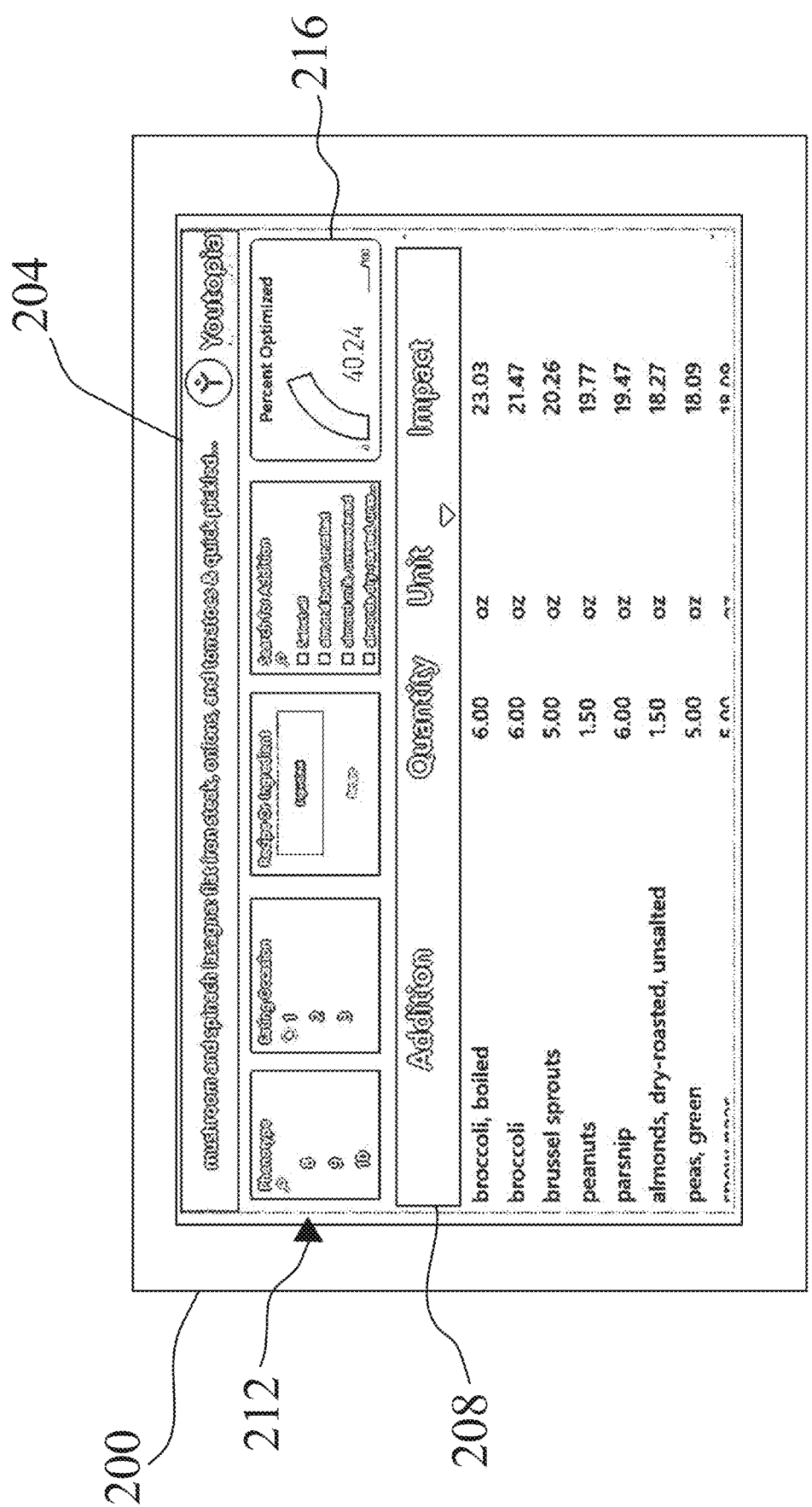
FIG. 2 illustrates an exemplary embodiment of a GUI.

Referring now to FIG. 2, an exemplary embodiment of a GUI 200 is presented. GUI 200 may include GUI 124 as described above with reference to FIG. 1. In some embodiments, GUI 200 may be displayed through, but not limited to, smartphones, tablets, laptops, monitors, and/or other display devices. GUI 200 may include meal title 204. A "meal title" as used in this disclosure is a name of a meal. Meal title 204 may be displayed at a top, bottom, and/or side portion of GUI 200. In some embodiments, meal title 204 may display a name of one or more meals. GUI 200 may display ingredient listing 208. An "ingredient listing" as used in this disclosure is a data set of one or more edible items. Ingredient listing 208 may include one or more base ingredients of a recipe, additional ingredients of a recipe, alternative ingredients of a recipe, and the like, without limitation. In some embodiments, ingredient listing 208 may be displayed in a square grid having one or more columns and/or one or more rows. Ingredient listing 208 may include a listing of additional ingredients, base ingredients, quantity of ingredients, unit of measurement of ingredients, and/or an impact score of an ingredient. In some embodiments, GUI 200 may display one or more recommended and/or additional ingredients through ingredient listing 208. Recommended and/or additional ingredients may be calculated by apparatus 100 as a function of user data, recipe data 104, and/or impact factors 116. In some embodiments, GUI 200 may include meal factors 212. A "meal factor" as used in this disclosure is one or more parameters of making a meal. Meal factors may include, but are not limited to, phenotypes, eating occasions, recipes and/or ingredients, additional ingredients, and/or optimization meter 216. An "eating occasion" as used in this disclosure is a temporal element of a meal. A temporal element of a meal may include, without limitation, a first meal, second meal, third meal, snack, breakfast, lunch, dinner, and the like. GUI 200 may display an indicator of a current eating occasion out of a plurality of eating occasions. GUI 200 may display one or more phenotypes that a meal of meal title 204 may be compatible with. For instance, and without limitation, GUI 200 may display meal factors 212 which may include a grouping of phenotype 8, phenotype 9, and/or phenotype 10, which may be biologically compatible with a meal of meal title 204, such as mushroom and spinach lasagna, flat iron steak, onions, and tomatoes.

Still referring to FIG. 2, in some embodiments, GUI 200 may display one or more levels of optimization meter 216. An "optimization meter" as used in this discourse is a graphical element showing a portion of a maximum value. Optimization meter 216 may display one or more numbers, values, gauges, and the like, without limitation. Optimization meter 216 may be generated by apparatus 100 as a function of user data and/or impact factors 116. For instance and without limitation, optimization meter 216 may display a gauge in a shape of a half circle being 40.24% full, which may indicate a current meal represented in meal title 204 is 40.24% optimized. Optimization meter 216 may display one or more colors which may represent one or more levels of optimization. For instance, and without limitation, optimization meter 216 may display a red color of a gauge indicating a low optimization percentage, such as 40.24%. Apparatus 100 may determine an optimization percentage through comparing one or more phenotypes with one or more ingredients, impact factors, user goals, and the like.

Figure 3:
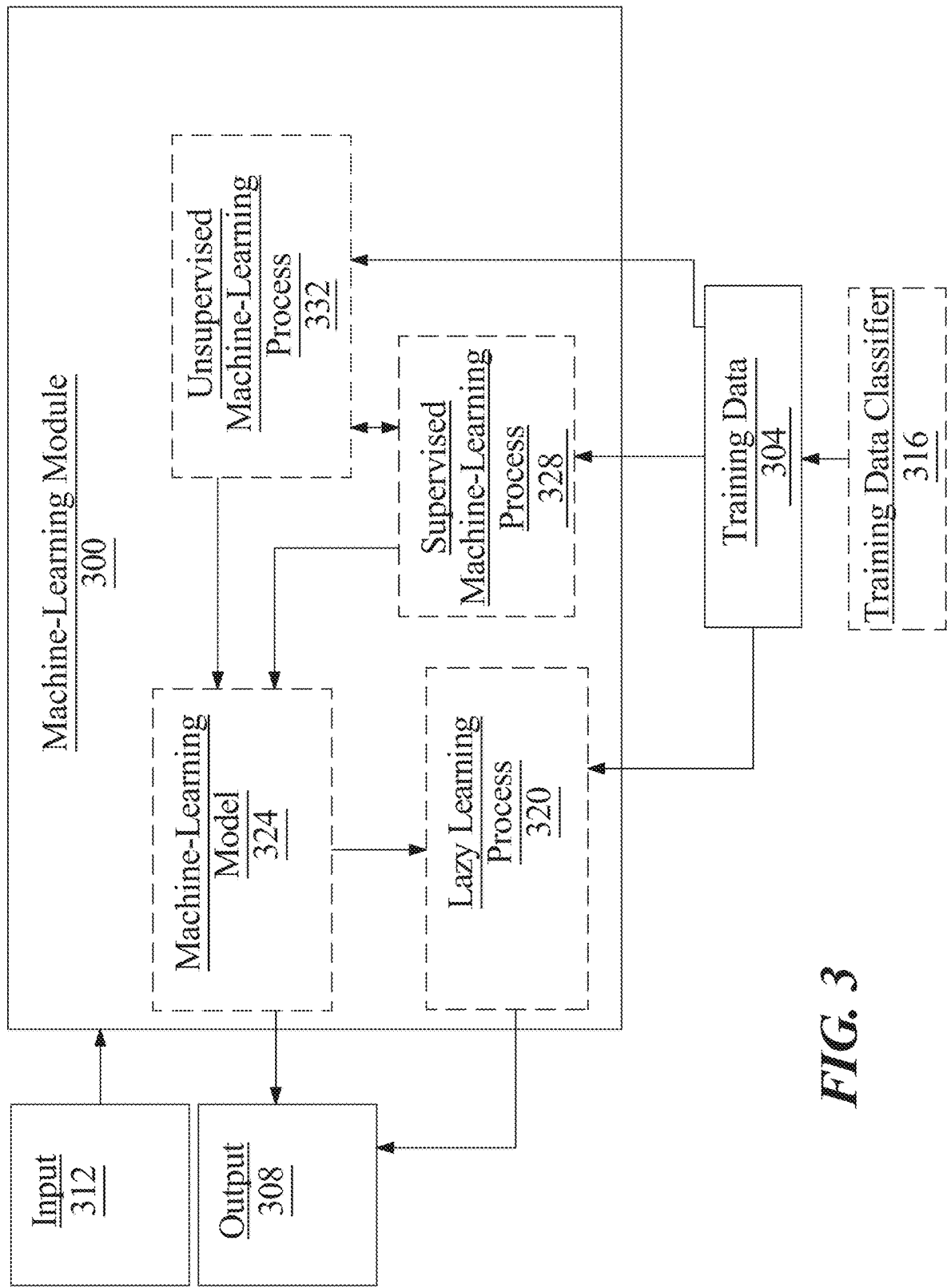
FIG. 3 is an exemplary embodiment of a machine learning model.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example inputs may include recipe data and outputs may include impact factors.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to impact factors, macronutrients, micronutrients, and the like.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include recipe data as described above as inputs, impact factors as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Figure 4:
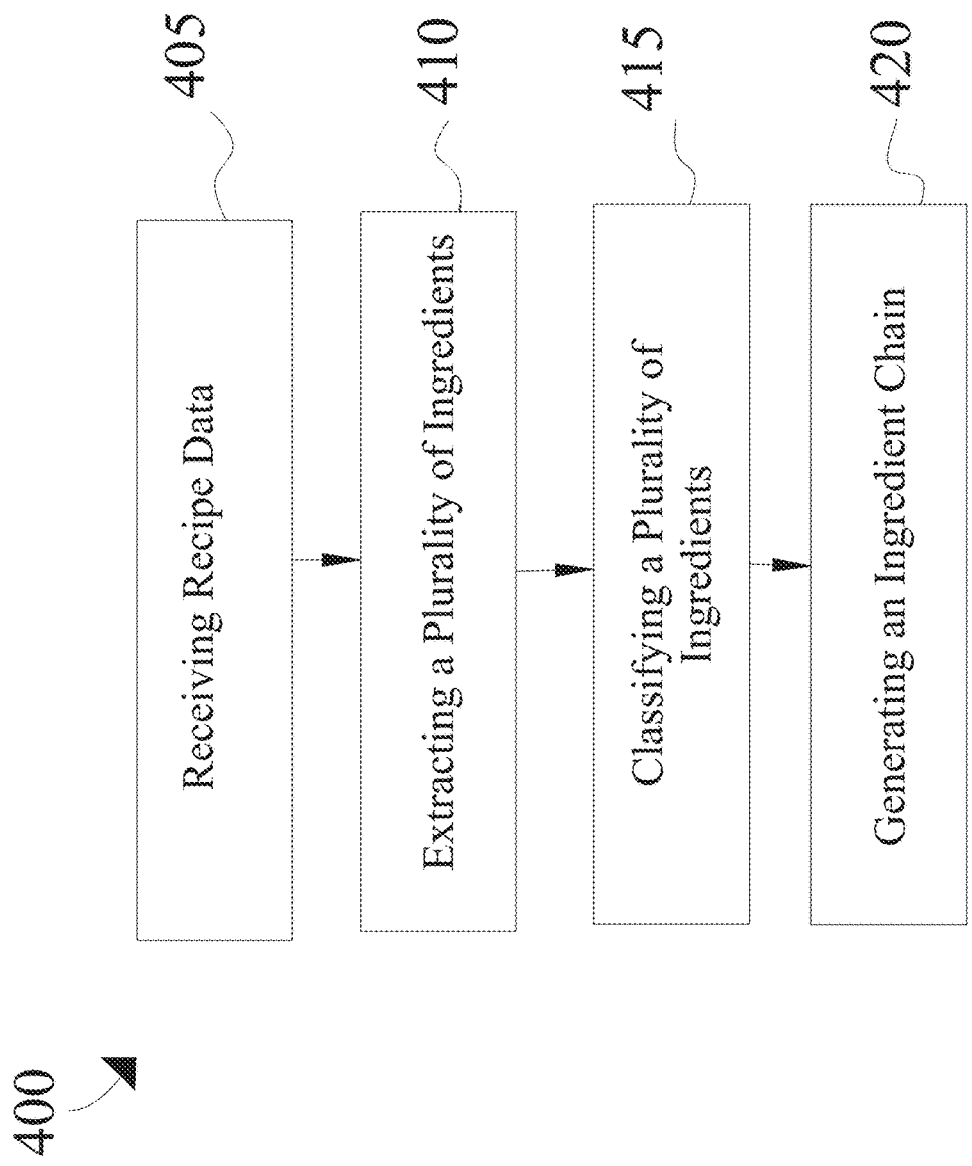
FIG. 4 is a flowchart of a method of generating an ingredient chain.

Referring now to FIG. 4, a method 400 of generating an ingredient chain is presented. At step 405, method 400 includes receiving, via at least a processor, recipe data from a user. In some embodiments, recipe data may be received through user input, external computing devices, and/or other forms of input. In some embodiments, recipe data may include meal idIdentifications. Generating an ingredient chain may include generating a web query, which may include a web crawler function. This step may be implemented as described above with reference to FIGS. 1-3, without limitation.

Still referring to FIG. 4, at step 405, method 400 includes extracting, via at least a processor, a plurality of ingredients from recipe data. Extracting may include using a language processing module. This step may be implemented as described above with reference to FIGS. 1-3, without limitation.

Still referring to FIG. 4, at step 410, method 400 includes classifying, via at least a processor and utilizing an ingredient classifier, a plurality of ingredients to a plurality of impact factors. Classifying may include identifying a plurality of constraints as a function of an identification of meals. In some embodiments, classifying a plurality of ingredients may include scoring a plurality of nutrients of the plurality of ingredients based on impact factors. Scoring may include generating an objective function. In some embodiments, classifying may include identifying a plurality of constrains as a function of a plurality of identifications of meals. This step may be implemented as described above with reference to FIGS. 1-3, without limitation.

Still referring to FIG. 4, at step 405, method 400 includes generating, via at least a processor, and as a function of impact factors, an ingredient chain for a user. In some embodiments, generating an ingredient chain may include determining a nutrition target range. In some embodiments, generating an ingredient chain may include generating an optimization score of a plurality of ingredients and display the optimization score of the plurality of ingredients through a graphical user interface (GUI). This step may be implemented as described above with reference to FIGS. 1-3, without limitation.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
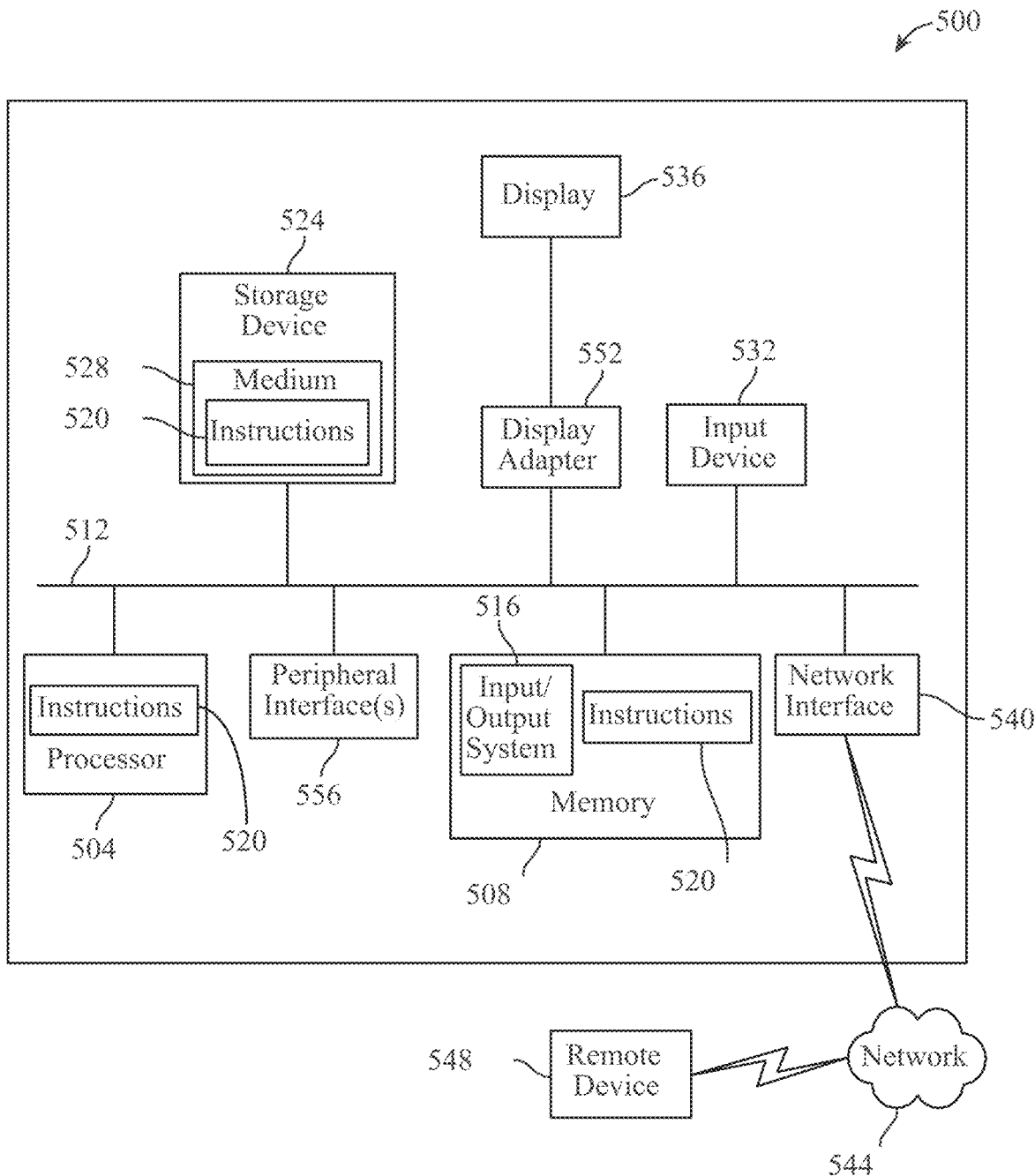
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Processor 504 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 504 may be organized according to Von Neumann and/or Harvard architecture as a non-limiting example. Processor 504 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 508 may include various components (e.g., machine-readable media) including, but not limited to, a random-access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for generating an ingredient chain, comprising:
    at least a processor; and a memory communicatively connected to the processor, the memory containing instructions configuring the at least a processor to:
    receive recipe data from a user;
    extract, from the recipe data, a plurality of ingredients;

determine an additional ingredient as a function of the plurality of ingredients;

wherein the additional ingredient is determined as a function of a geographic availability of the additional ingredient;

classify, utilizing an ingredient classifier, the plurality of ingredients and the additional ingredient to a plurality of impact factors; and generate, as a function of the impact factors, a first ingredient chain for a user.

2. The apparatus of claim 1, wherein determining the additional ingredient comprises:

identifying the additional ingredient as a function of the plurality of ingredients;

communicating the additional ingredient to the user; and receiving a response from the user.

3. The apparatus of claim 1, wherein the memory contains instructions configuring the at least a processor to:

generate, as a function of the impact factors, a second ingredient chain for the user;

determine an ingredient chain ranking as a function of a geographic availability of ingredients of the first ingredient chain and the second ingredient chain; and display to the user the ingredient chain ranking.

4. The apparatus of claim 1, wherein generating the first ingredient chain comprises:

categorizing the first ingredient chain to an ingredient chain category;

receiving a category preference from the user; and comparing the ingredient chain category to the category preference.

5. The apparatus of claim 4, wherein categorizing the first ingredient chain to an ingredient chain category comprises:

training an ingredient chain category classifier on a training dataset including a plurality of example ingredient chains as inputs correlated to a plurality of example ingredient chain categories as outputs; and identifying an ingredient chain category as a function of the first ingredient chain using the ingredient chain category classifier.

6. The apparatus of claim 1, wherein the memory contains instructions configuring the at least a processor to receive a preparation time limit from the user, wherein the first ingredient chain is determined as a function of the preparation time limit.

7. The apparatus of claim 1, wherein the memory contains instructions configuring the at least a processor to receive a preparation skill datum from the user; wherein the first ingredient chain is determined as a function of the preparation skill datum.

8. The apparatus of claim 1, wherein the memory contains instructions configuring the at least a processor to:

receive an ingredient chain selection datum from a user; and store an ingredient chain associated with the ingredient chain selection datum in a database as a function of the ingredient chain selection datum.

9. The apparatus of claim 1, wherein the recipe data comprises a list of ingredients possessed by the user.

10. A method of generating an ingredient chain, the method comprising:

using at least a processor, receiving recipe data from a user;

using at least a processor, extracting, from the recipe data, a plurality of ingredients;

using at least a processor, determining an additional ingredient as a function of the plurality of ingredients;

wherein determining the additional ingredient is determined as a function of a geographic availability of the additional ingredient;

using at least a processor, classifying, utilizing an ingredient classifier, the plurality of ingredients and the additional ingredient to a plurality of impact factors; and using at least a processor, generating, as a function of the impact factors, a first ingredient chain for a user.

11. The method of claim 10, wherein determining the additional ingredient comprises: identifying the additional ingredient as a function of the plurality of ingredients; communicating the additional ingredient to the user; and receiving a response from the user.

12. The method of claim 10, further comprising: using at least a processor, generating, as a function of the impact factors, a second ingredient chain for the user; using at least a processor, determining an ingredient chain ranking as a function of a geographic availability of ingredients of the first ingredient chain and the second ingredient chain; and using at least a processor, displaying to the user the ingredient chain ranking.

13. The method of claim 10, wherein generating the first ingredient chain comprises: categorizing the first ingredient chain to an ingredient chain category; receiving a category preference from the user; and comparing the ingredient chain category to the category preference.

14. The method of claim 13, wherein categorizing the first ingredient chain to an ingredient chain category comprises: training an ingredient chain category classifier on a training dataset including a plurality of example ingredient chains as inputs correlated to a plurality of example ingredient chain categories as outputs; and identifying an ingredient chain category as a function of the first ingredient chain using the ingredient chain category classifier.

15. The method of claim 10, further comprising using at least a processor, receiving a preparation time limit from the user, wherein the first ingredient chain is determined as a function of the preparation time limit.

16. The method of claim 10, further comprising using at least a processor, receiving a preparation skill datum from the user; wherein the first ingredient chain is determined as a function of the preparation skill datum.

17. The method of claim 10, further comprising: using at least a processor, receiving an ingredient chain selection datum from a user; and using at least a processor, storing an ingredient chain associated with the ingredient chain selection datum in a database as a function of the ingredient chain selection datum.

18. The method of claim 10, wherein the recipe data comprises a list of ingredients possessed by the user.

* * * * *